| United States Patent [19] | [11] | 4,135,977 |
|---|---|---|
| Horikoshi et al. | [45] | Jan. 23, 1979 |

[54] PROCESS FOR PRODUCTION OF CYCLODEXTRIN

[75] Inventors: Koki Horikoshi, Tokyo; Nobuyuki Nakamura, Kunitachi, both of Japan

[73] Assignee: Rikagaku Kenkyusho, Wako, Japan

[21] Appl. No.: 843,263

[22] Filed: Oct. 18, 1977

Related U.S. Application Data

[63] Continuation-in-part of Ser. No. 584,653, Jun. 6, 1975, abandoned.

[30] Foreign Application Priority Data

Jun. 20, 1974 [JP] Japan .................................. 49-70377

[51] Int. Cl.$^2$ ............................................. C12D 13/02
[52] U.S. Cl. ......................................... 195/7; 195/13; 195/31 R
[58] Field of Search ....................... 195/4, 7, 13, 31 R, 195/66 R, 62, 65

[56] References Cited

U.S. PATENT DOCUMENTS

| 3,425,910 | 2/1969 | Armbruster et al. | 195/31 R |
| 3,806,415 | 4/1974 | Hayes | 195/31 R |
| 3,923,598 | 12/1975 | Horikoshi | 195/31 R |

OTHER PUBLICATIONS

Suetsugi et al., "Kinetic Studies on the Hydrolysis of $\alpha, \beta$, and $\gamma$–cyclodextrins", Chemical Abstracts, vol. 81, No. 19, p. 211 (1974), Abs. No. 116567s.

*Primary Examiner*—Thomas G. Wiseman
*Attorney, Agent, or Firm*—Bucknam and Archer

[57] ABSTRACT

This invention provides a novel process for producing cyclodextrin by reacting cyclodextrin glycosyl transferase having an optimum pH on the alkaline side with gelatinized starch. According to this invention, cyclodextrin can be obtained in the form of a pure crystal in a high yield by reacting a glucomylase with the reaction mixture liquid formed by the above enzymatic reaction to decompose unreacted starch, concentrating the liquid, adding a small amount of cyclodextrin as a seed crystal and recovering the precipitated cyclodextrin.

3 Claims, 4 Drawing Figures

PROCESS FOR PRODUCTION OF CYCLODEXTRIN

CROSS-REFERENCE

This is a continuation-in-part of Ser. No. 584,653 filed June 6, 1975, now abandoned.

FIELD OF THE INVENTION

This invention refers to an improvement of the method for preparing cyclodextrin disclosed in United States Application No. 452,139, now U.S. Pat. No. 3,923,598, and according to this invention there is provided an industrially advantageous process thereof.

More specifically, in accordance with this invention, there is provided a novel process for producing cyclodextrin which comprises reacting a cyclodextrin glycosyl-transferase having an optimum pH on the alkaline side (hereinafter referred to as "the present enzyme") with starch at a pH of 6.0 to 10.5, adding a glycoamylase to the resulting reaction mixture liquid to decompose unreacted starch, concentrating the liquid to form a concentrate containing cyclodextrin at a content of at least 40%, and adding a small amount of cyclodextrin as a seed to the concentrate to precipitate cyclodextrin such as mentioned below.

That is, the present invention deals with a novel process for producing cyclodextrin comprising using "gelatinized starch" as a starch, using an enzyme having an appropriate pH value on the alkaline side produced by a microorganism selected from Bacillus sp. No. 38-2 (ATCC 21594), Bacillus sp. No. 135 (ATCC 21595), Bacillus sp. No. 169 (ATCC 21594), Bacillus sp. No. 13 (ATCC 31006) and Bacillus sp. No. 17-1 (ATCC 31007) as a cyclodextrin-glycosyltransferase, and crystallizing the cyclodextrin by adding, as a seed, a small amount of crystals of cyclodextrin to a concentrated liquid containing more than about 40% of cyclodextrin, without using a precipitating agent.

The cyclodextrin prepared according to the process of this invention has the following structure:

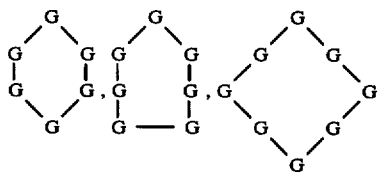

and so on.

Accordingly, the cyclodextrin prepared according to the process of this invention α-, β- and γ-cyclodextrins. Such dextrin is valuable as a sweetening substance or a substitute for gum arabic and so on.

DESCRIPTION OF THE PRIOR ART

Cyclodextrin is a decomposition product of starch obtained by hydrolyzing starch with an amylase, and it is generally known as a linear substance. It is known in the art that cyclodextrin (Schardlinger dextrin) is produced by Bacillus macerans (see "Enzyme Handbook" compiled by Shiro Akabori and published by Asakura Shoten, Tokyo, Japan in 1966). This cyclodextrin has heretofore been prepared by a method comprising adding calcium carbonate and water to fresh potato, sterilizing the mixture, inoculating the mixture with Bacillus macerans to cultivate the microorganism, removing cells from the culture medium to obtain an enzyme liquid, adding the enzyme liquid to a starch liquid formed by adding starch to water and dispersing it therein to cause the enzyme to act on starch, and adding an organic solvent such as tetrachloroethane, trichloroethylene and acetone to the reaction mixture liquid to precipitate the resulting cyclodextrin.

In view of the efficiency for collection of cyclodextrin, it is desired that the enzymatic reaction is carried out while maintaining a high concentration of the starch liquid. However, when the starch concentration is elevated, it is difficult to obtain a homogeneously dispersed starch liquid, and a complete enzymatic action cannot be expected. When a liquid having a low concentration is used, complicated means or an expensive reagent should be employed for separation of cyclodextrin, and various economical disadvantages are brought about. For overcoming these defects, there has been proposed in Japanese Patent Publication No. 2380/1971 a method in which a high concentration starch liquid is formed by liquefying starch in the starting starch liquid by addition of a small amount of an α-amylase, by action of an acid or according to other conventional technique and the amylase produced from Bacillus macerans is caused to act on the high concentration starch liquid to produce cyclodextrin.

We proposed in Japanese Patent Application No. 31680/1973 and 136664/1973 and U.S. Ser. No. 452,139 a novel processes for producing cyclodextrin by using amylases having an optimum pH on the alkaline side and a high temperature stability. These methods can overcome the defects of the conventional methods utilizing the enzymatic activity of the enzyme produced from Bacillus macerans, and can advantageously provide cyclodextrin on an industrial scale. However, in each of these methods, collection of cyclodextrin is performed by precipitating the product by using an organic solvent such as tetrachloroethane, trichloroethylene and acetone. Since these precipitants are expensive and toxic, use of these precipitants is not desirable.

Therefore, in order to overcome these defects, we have provided an improved process for producing cyclodextrin in which an expensive and toxic organic solvent used in the conventional methods need not be used for recovering cyclodextrin from the reaction liquid formed by reacting the above enzyme with a starch liquid.

U.S. Pat. No. 3,425,910, on the other hand, is related to a method which converts a starch liquefied into a D.E. (Dextrose Equivalent) of 0.5 to 20 into the cyclodextrin by acting said starch upon a cyclodextrin-transglycosylase. The differences in fundamental setups and the effects between the Patent and the present invention are mentioned below.

"Liquefied starch" means that it is one obtained by liquefying starch using acid or α-amylase and it contains a substantial amount of reducing sugar. Therefore it is one hydrolyzed to a predetermined D.E. as shown in the citation.

On the contrary, "gelatinized starch" used in the present invention means starch which is not hydrolyzed at all and is in a state of dispersion in water in a form of colloid, and it contains a very small amount of reducing sugar (less than 0.5%), and it is in a state of gel by destruction of starch particles.

Conventional methods employing a gelatinized starch invited retrogradation during the enzymatic action by an acidic to neutral amylase, causing the formation of the cyclodextrin to be reduced remarkably, and eventually making it necessary to use a liquefied starch. Even when the liquefied starch was used, however, low molecular weight reducing saccharides were formed making it hard to obtain good results.

There was, therefore, eventually proposed a method by which the D.E. of the starch was set at 0.5 to 20, a precipitating agent such as trichloroethylene, toluene and the like were added to include the cyclodextrin to precipitate the cyclodextrin advantageously. However, since the precipitating agent itself has toxicity. (Example I of the Patent employs toluene in an amount of 5 ml per 100 ml of the conversion liquor, which is 5% equivalent), and the cyclodextrin once formed continuously during the reaction undergoes ring-opening and converts itself into other glycosyl residues, it was eventually impossible to obtain good results.

In addition to the above, the acidic or neutral amylase ordinarily used in the art is unstable to heat and the enzymic reaction thereof must be carried out at a temperature of about 40 to 50° C. and the use of a higher temperature causes retrogradation and must be avoided.

On the contrary, the present enzymes can act directly on gelatinized starch dissolved in aqueous NaOH without liquefying to advantageously produce, separate and crystallize cyclodextrin. This is very beneficial over the prior art.

In the present invention the enzyme reaction is carried on gelatinized starch using the present enzyme, the reaction liquid is concentrated to a concentrate containing cyclodextrin in an amount higher than 40%, then the unreacted substance is decomposed and further cyclodextrin is advantageously separated and crystallized by adding to said concentrate a small amount of crystal of cyclodextrin as seed. The present invention possesses the following advantageous points, namely the present alkaliamylase can carry out the enzyme reaction at a temperature higher than 55° C. without occurrence of any retrogradation at such higher temperature, and further can avoid the use of a toxic precipitants such as trichloroethylene in the use of the crystallizing method in which cyclodextrin is advantageously crystallized by the addition of seeds of cyclodextrin. On the contrary, we cannot obtain crystal of cyclodextrin by the method disclosed in the prior arts, because by the prior art method, the obtained cyclodextrin contains more than 60% of alpha-cyclodextrin, alpha-cyclodextrin being difficultly crystallizable under the effect of crystals of cyclodextrin.

Therefore the present invention is novel and patentable because this invention represents a novel technical method for making the use of gelatinized starch possible, and has patentable features because the enzyme reaction is carried out by the present enzyme on gelatinized starch in a pH of 6–10.5, especially 9.0–10.5, the reaction liquor is concentrated and seeds of crystallized cyclodextrin are added to said concentrated liquor to crystallize out cyclodextrin in a good yield.

Next, the reason why the cyclodextrin of high purity can be obtained in high yields by the method of the present invention by adding a seed of cyclodextrin, but without using the precipitating agent of said patent, is because the use of the cyclodextrin-glycosyltransferase (enzyme produced by the aforementioned microorganism) having an appropriate pH value on the alkaline side is an essential requirement for the present invention.

The cyclodextrin-glycosyltransferase of the method of the present invention forms the cyclodextrin advantageously by the action of the gelatinized starch. And by adding the seed of cyclodextrin in small amounts to the concentrated liquid, it is possible to precipitate and sediment the cyclodextrin in pure form.

In this regard, the comparative test 2 will clarify that results superior to the results of the patent are obtained even when the cyclodextrin-glycosyltransferase of the method of the present invention is reacted using the liquefied starch of the patent to form the cyclodextrin and even using a precipitating agent according to the method of the said Patent. The feature of the method of the present invention is that the cyclodextrin is obtained in higher purity and higher yield than that of the patent by reacting the gelatinized starch without using the precipitating agent.

An object of this invention is to provide an improved process for producing cyclodextrin by reacting the present enzyme with starch.

Another object of this invention is to provide a novel process in which cyclodextrin is recovered in a high yield and easily from the liquid formed by the above enzymatic reaction.

The enzyme to be used in the process of this invention is a cyclodextrin glycosyl transferase having an optimum pH on the alkaline side, which is a fermentation product of a microorganism growing only in an alkaline medium.

As such microorganisms, there can be mentioned, for example, Bacillus sp. No. 38-2, Bacillus sp. No. 135 and Bacillus sp. No. 169 that were isolated from soils in Wako city, Saitama prefecture, Japan, by inventors and Bacillus sp. No. 13 and Bacillus sp. No. 17-1 that were isolated from soils in Karuizawa city, Nagano prefecture, Japan, by inventors, these microorganisms having been mentioned in the Japanese Patent Application No. 31,680/1973 and 136,664/1973 and U.S. Ser. No. 452,139. In this invention, microorganisms that can be used are not limited to those mentioned above, but any of microorganisms that can produce the alkaline amylase of this invention having a capability of producing cyclodextrin and natural or artificial mutants thereof can be used in this invention.

The strains identified as said Bacillus sp. No. 38-2, Bacillus sp. No. 135, Bacillus sp. No. 169, Bacillus sp. No. 13 and Bacillus sp. No. 17-1 were deposited with the American Type Culture Collection (ATCC) at 12301 Parklawn Drive, Rockville, Maryland 20852 U.S.A. as ATCC access numbers 21783, 21595, 21594, 31006 and 31007, in unrestricted condition permitting the public to have full access to the cultures, as of Mar. 27, 1972, Aug. 19, 1970, Aug. 19, 1970, Feb. 21, 1974 and Feb. 21, 1974, respectively. We shall rewrite hereinbelow the characteristics of these microorganisms and enzymes which was disclosed in the specification of U.S. Ser. No. 452,139 (U.S. Pat. No. 3,923,598) and Japanese applications above mentioned.

Either solid or liquid media can be used for culturing these strains, but it is indispensable that the culture medium should be an alkaline medium containing a carbonate. More specifically, a medium formed by adding a carbonate to a medium comprising components necessary for growth of microorganisms, such as a carbon source, a nitrogen source and inorganic salts, for example, a culture medium formed by adding a carbonate to a medium comprising soluble starch, peptone, yeast extract, $K_2HPO_4$, $MgSO_4.7H_2O$ etc., is used in this invention.

Culturing of the above-mentioned microorganisms is performed aerobically under shaking or under agitation with air current. For example, the microorganism is cultured under shaking at 30 to 37° C. for 24 to 96 hours, and after the culturing cells are removed and the resulting enzyme is precipitated or salted out by an organic solvent or a salt such as ammonium sulfate after or without neutralization of the added carbonate with acetic acid or a similar acid. The recovered enzyme is dehydrated and dried to obtain a powder of a crude enzyme for production of cyclodextrin.

The intended product of this invention, namely cyclodextrin, can be prepared by using the so obtained enzyme according to the following process. More specifically, starch is gelatinized, the pH of the gelatinized starch is adjusted to 6.0 to 10.5, especially 9.0 to 10.5, and the present enzyme is added thereto. The mixture is allowed to stand still for a suitable time, insoluble substances are removed, and the intended cyclodextrin can be collected in a high yield without use of a precipitant by adding a commercially available glucoamylase to the liquid mixture obtained by reacting the present enzyme with starch, concentrating the resulting mixture and adding a small amount of cyclodextrin as a seed to the concentrate.

More specifically, in accordance with a preferred embodiment of this invention, a process for collecting cyclodextrin from a reaction mixture liquid obtained by causing a liquid of the present enzyme to act on starch, which comprises adding a glucoamylase to said reaction mixture liquid to decompose unreacted starch, concentrating the mixture to form a concentrate containing cyclodextrin at a concentration of at least about 40%, and adding a small amount of cyclodextrin as a seed to the concentrate to precipitate crystals of the intended product. This process is very advantageous from the industrial viewpoint.

DESCRIPTION OF THE PREFERRED EMBODIMENTS

Figure 1:
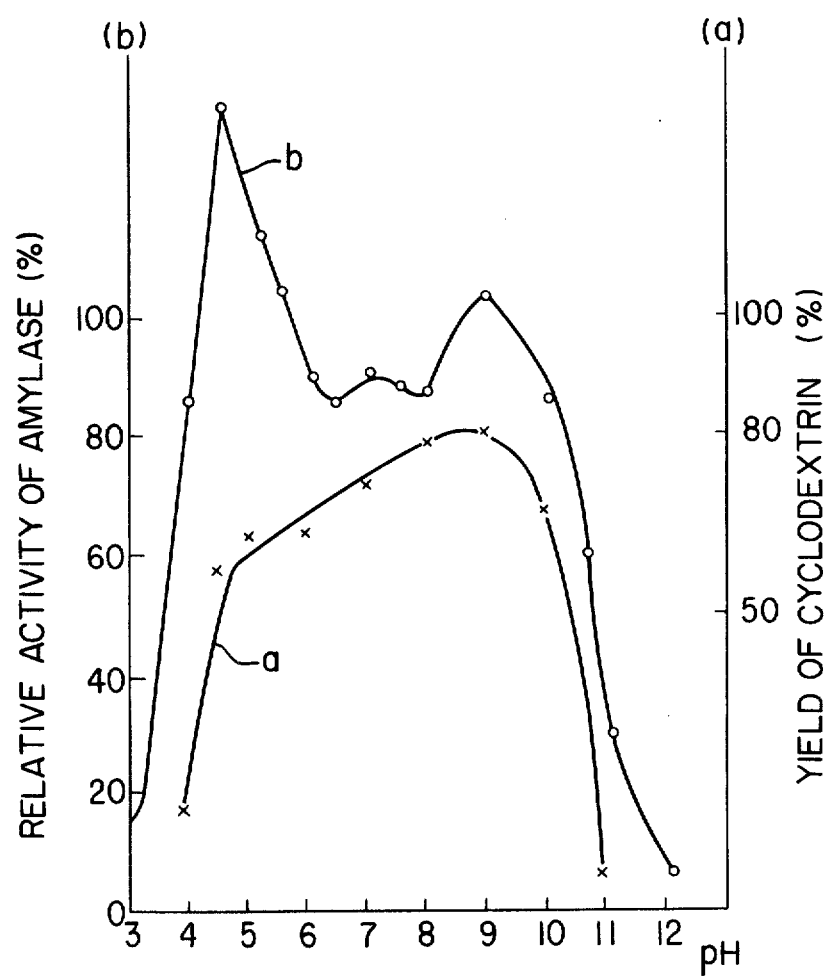
FIG. 1 illustrates the relation (curve a) between the ratio of production of cyclodextrin by the enzyme of this invention (fermentation product of Bacillus sp. No. 38-2 (ATCC 21783)) and the pH, and the relation (curve b) between the amylase activity of said enzyme and the pH.

Characteristics and properties of those microorganisms will be disclosed below. We have examined the properties and characteristics of above described species according to the methods described in "Aerobic Spore-forming Bacteria" by Nathan R. Smith, R. E. Gordon and F. E. Clark (United States Department of Agriculture, November 1952) and "Bergey's Manual of Determinative Bacteriology" (1957). Results of examination are shown as follows:

(1) Bacillus sp. No. 38-2 (ATCC 21783)

(a) Growth on Various Media:

Table 1

| | Medium | Growth at pH 7 | Growth at pH 10 |
|---|---|---|---|
| 1. | Bouillon | Growth scant | Very poor growth |
| 2. | Bouillon-agar | Growth scant | Very poor growth |
| 3. | Glucose-bouillon | Poor growth | Turbid, good growth |
| 4. | Glucose-bouillon-agar | Poor growth | Good growth |
| 5. | Gelatin medium | — | Growth, liquefied |
| 6. | Aqueous pepton | — | Growth |
| 7. | Potato medium | Growth scant | Good growth |

(b) Microscopic Morphology:

Size of the microorganism is $0.5$–$0.6\mu \times 2.0$–$3.0\mu$. The spore which is formed near the end of the cell is oval and has a size of $0.9$–$1.0\mu \times 1.2$–$1.5\mu$; The sporangium is definitely swollen; The bacteria have pertrichous flagella and are motile and form motile collonies; Gram positive and non-acid-fast.

It grows very well on an alkaline medium comprising soluble starch, yeast extract, peptone, $K_2HPO_4$ and $MgSO_4.7H_2O$ and containing 1% $Na_2CO_3$ whereas growth on any neutral medium is poor.

(c) Physiological Properties:

1. Optimum Growth Condition:

pH: around 10
   Temperature: 37°–40° C.
   Aerobic

2. Conditions under which the microorganism grows:

pH: 7.5–11
   Temperature: up to 45° C.

3. Voges-Proskauer reaction: Positive
4. Nitrate: Reduced
5. Catalase reaction: Positive
6. Gelatin, Casein: Liquefied
7. Hydrolysis of Starch: Positive
8. Utilization of Citrate: Utilized but poor
9. Utilization of Ammonium Salt: Utilized
10. Growth in 7% Sodium Chloride Solution: Poor
11. Growth on Glucose-nitrate Medium: Growth
12. Growth under Anaerobic Condition: Growth
13. Growth on Glucose-asparagine Medium: Growth
14. Production of Indole: Negative (d) Utilization of Carbon Source:

Glucose, fructose, xylose, sucrose, maltose, lactose and arabinose are utilized, by galactose, trahalose and inulin are not utilized. Production of acid is observed.

(2) Bacillus sp. No. 135 (ATCC 21595)

(a) Growth on Various Media:

Table 2

| Media | Growth at pH 7 | Growth at pH 10 |
|---|---|---|
| 1. Bouillon | Poor growth | Poor growth |
| 2. Bouillon-agar | Poor growth | Fairly good growth |
| 3. Glucose-Bouillon | Very poor growth | Very good growth |
| 4. Glucose-Bouillon agar | Growth | Very good growth |
| 5. Gelatine medium | — | Growth |
| 6. Aqueous peptone | — | Growth |
| 7. Potato medium | Growth | Good growth |

(b) Microscopic Morphology:

Size of the microorganism is $0.6-0.8\mu \times 2.5-4\mu$; The sporangium is slight swollen and the spore is oval having size of $1.0-1.2\mu \times 1.5-1.8\mu$. The microorganism has pertrichous flagella and motile.

This Bacillus grows very well on an alkaline medium comprising soluble starch, yeast extract, peptone, $K_2HPO_4$, $MgSO_4.7H_2O$ and containing 1% of $Na_2CO_3$, and appears white. The characteristic of the species is that is grows very well on alkaline medium, though grows a little on neutral medium.

(c) Physiological Properties:

1. Optimum Growth Condition:

pH: around 10
    Temperature: 37°–40° C.
    Aerobic

2. Conditions under which the bacteria can grow:
    pH: 7–11
    Temperature: up to 42° C.
    Aerobic 3. Gram Stainability: Positive
4. Voges-Proskauer Reaction: Positive
5. Nitrate: Reduced
6. Catalase: Positive
7. Gelatine and Casein: Liquefied
8. Hydrolysis of Starch: Positive
9. Utilization of Citrate: Not utilized
10. Utilization of Ammonium salt: Utilized
11. Growth in 7% NaCl Solution: No detected
12. Growth on Glucose-Nitrate Medium: Growth scant
13. Growth under Anaerobic Condition: Detected
14. Production of Gas in Nitrate Medium under Anaerobic Condition: No produced
15. Growth on Glucose-Asparagine Medium: Growth (d) Utilization of Carbon Source:

Glucose, mannose, salicin, cellobiose, lactose, sucrose, arabinose, mannitol and xylose are utilized, but production of acid can not be observed, because a lot of carbonate is used.

(3) Bacillus sp. No. 169 (ATCC 21594)

(a) Growth on Various Media:

Table 3

| Media | Growth at pH 7 | Growth at pH 10 |
|---|---|---|
| 1. Bouillon | Growth scant | Poor growth |
| 2. Bouillon-agar | Growth scant | Poor growth |
| 3. Glucose-Bouillon | Growth scant | Turbid, good growth |
| 4. Glucose-Bouillon-Agar | Growth scant | Good growth |
| 5. Gelatine medium | — | Good growth liquefied |
| 6. Peptone water | — | Growth |
| 7. Potato medium | Poor growth | Good growth |

(b) Microscopic Morphology:

Size of the microorganism is $0.5-0.6\mu \times 2-3\mu$; The sporangium is slightly swollen and the spore is oval having a size of $1.0-1.2\mu \times 1.3-1.7\mu$. The microorganism has pertrichous flagella and is motile. It grows very well on an alkaline medium comprising soluble starch, yeast extract, peptone, $K_2HPO_4$ and $MgSO_4.7H_2O$ and containing 1% $Na_2CO_3$ but it hardly grows on any neutral medium.

(c) Physiological Properties:

1. Optimum Growth Condition:
    pH: 8–10
    Temperature: 37°–40° C.
    Aerobic 2. Conditions under which the bacteria can grow:
    pH: 7.5–11
    Temperature: up to 45° C.
    Aerobic 3. Gram stainability: Positive, Changeable
4. Voges-Proskauer reaction: Positive
5. Nitrate: Reduced
6. Catalase reaction: Positive
7. Hydrolysis of gelatin and casein: Positive
8. Hydrolysis of starch: Positive
9. Utilization of citrate: Not utilized
10. Growth in 7% NaCl solution: Not growth
11. Growth on glucose-nitrate medium: Scant
12. Growth under anaerobic condition: Growth
13. Production of gas in nitrate medium under anaerobic condition: Not produced
14. Growth on glucose-asparagine medium: No growth
15. Production of indol: Negative (d) Utilization of Carbon Source:

Glucose, mannose, cellobiose, lactose, sucrose, mannitol and salicin are utilized very well, but arabinose and xylose are not utilized.

Production of acid cannot be determined since the medium contains a lot of carbonate.

(4) Bacillus sp. No. 13 (ATCC 31006)

(a) Growth on Various Media:

Table 4

| Medium | Growth at pH 7.0 | Growth at pH 10.0* |
|---|---|---|
| 1. Bouillon liquor | growth scant | Growth, turbid; and sediment; membranous |
| 2. Bouillon-agar | Growth scant | Circular, flat or raised; entire; smooth, brilliant surface, translucent, milky white |
| 3. Bouillon-agar slant | Growth scant | Spreading with dull edges and brilliant center; milky white translucent; no pigment |
| 4. Bouillon-gelatin thrust | Growth scant; no liquefaction of | Liquefied in layer |

Table 4-continued

| Medium | Growth at | |
|---|---|---|
| | pH 7.0 | pH 10.0* |
| | gelatin | |

*1% Na₂CO₃ is added to the medium in order to ad (b) Microscopic Morphology:

Size of the cell is 0.5–0.7μ × 2.0–4.0μ; oval spore is formed at the end of the cell; size of the spore is 1.3–1.4μ × 1.5–1.6μ; the sporangium is definitely swollen; the microorganism has pertrichous flagella and is motile. The gram stainability thereof is positive and the acid-fast test is negative.

Note: Above morphological observation has been made on a medium comprising 10 grams sodium carbonate, 5 grams peptone, 5 grams yeast extract, 20 grams starch, 1 gram K₂HPO₄, 0.2 gram MgSO₄.7H₂O, 15 grams agar and 1 liter water.

(c) Physiological Properties:

The following results have been observed on a media which has been described in "Aerobic Spore-forming Bacteria" by N. R. Smith et al., modified by adding 1% Na₂CO₃ respectively.
1. Nitrate: Reduced
2. Denitrogenation: Negative
3. Methyl red test: No change of color, due to basicity of the medium
4. Voges-Proskauer reaction: Positive
5. Production of indole: Negative
6. Production of hydrogen sulfide: Negative
7. Hydrolysis of starch: Utilized
8. Utilization of citric acid: Utilized
9. Utilization of nitrate and ammonium: Slightly utilized
10. Production of pigment: Negative
11. Catalase reaction: Positive
12. pH range for growth: 7.5–11
13. Temperature range for growth: up to 42° C.; optimum 37°–40° C.
14. Behavior to oxygen: Aerobic
15. Growth in 5% NaCl solution: Slightly growth (d) Utilization of Carbon Source:

Lactose, arabinose, xylose, glucose, mannose, inositole, fructose, galactose, maltose, sucrose, trehalose, mannitol, starch, sorbitol and glycerine are utilized, and acids are produced. Production of gas is not detected.

(5) Bacillus sp. No. 17-1(ATCC 31007)

(a) Growth on various media:

Table 5

| | Medium | Growth at | |
|---|---|---|---|
| | | pH 7.0 | pH 10.0* |
| 1. | Bouillon liquor | Scant | Growth, turbid and sediment; membranous |
| 2. | Bouillon-agar plane | Slightly growth | Circular, flat or raised; smooth, brilliant surface; translucent; milky white |
| 3. | Bouillon-agar slant | Slightly growth | Spreading; milky white, translucent, No pigment in medium |
| 4. | Bouillon-gelatin thrust | Scant No liquefaction | Liquefied as crater |

*1% Na₂CO₃ is added to the medium in order to regulate pH value to 10.0

(b) Microscopic Morphology:

The vegitative cell is a rod having a size of 0.5–0.7μ × 2.0–4.0μ. Oval spore is formed at subterminal. The size of a spore is 0.8–1.0μ × 1.2–1.5μ. The sporangium is definitely swollen. The microorganism has pertrichous flagella and is motile; gram positive and non acid-fast.

The above observation has been made on a medium comprising 10 grams sodium carbonate, 5 grams peptone, 5 grams yeast extract, 20 grams starch, 1 gram K₂HPO₄, 0.2 gram MgSO₄.7H₂O, 15 grams agar and 1 liter of water.

(c) Physiological Properties:

The following results have been observed on media described in "Aerobic Spore-forming Bacteria" by N. R. Smith et al., and modified by adding 1% Na₂CO₃ respectively.
1. Nitrate: Reduced
2. Denitrogenation: Negative
3. Methyl Red Reaction: No change of colour, due to basicity of the medium
4. Vogel-Proskauer reaction: Negative
5. Production of indole: Negative
6. Production of hydrogen sulfide: Negative
7. Hydrolysis of starch: Positive
8. Utilization of citric acid: Utilized very well
9. Utilization of nitrate and ammonium salt: Utilized very well
10. Production of pigment: Not produced
11. Catalase reaction: Positive
12. pH range for growth: 7–11
13. Temperature range for growth: up to 42° C.; optimum: 37°–40° C.
14. Behavior to oxygen: Aerobic
15. Growth in 7% NaCl solution: Growth well (d) Utilization of Carbon Source:

Lactose, arabinose, xylose, glucose, mannose, inocitole, fructose, galactose, maltose, sucrose, trehalose, mannitole, starch, sorbitol and glycerine are utilized and acids are produced. Production of gas has not been detected.

Studying the bacteriological properties disclosed above, Bacillus species No. 38-2, Bacillus species No. 135, Bacillus species No. 169, Bacillus species No. 13 and Bacillus species No. 17-1 belong to the Bacillus genus, because those microorganisms are an aerobic and spore-forming bacteria respectively.

Further we found that for identification of these microorganisms, Bacillus polymixa, Bacillus macerans and Bacillus circulans shall be selected as known species for comparison, because every sporangium thereof is definitely swollen. Even our new microorganisms are similar in some properties to the known species, they are entirely different in characteristic properties, particularly by the fact that the optimum pH value of our microorganisms reside in alkaline side, whereas that of known species in neutral.

The following Table 6 shows various characteristic properties of Bacillus polymixa, Bacillus macerans and Bacillus circulans (known species) as well as Bacillus sp. No. 38-2, Bacillus sp. No. 135, Bacillus sp. No. 169, Bacillus sp. No. 13 and Bacillus sp. No. 17-1 (new species).

Table 6

| Bacillus species | Growth in 5% NaCl | Utilization of citric acid | Utilization of nitrate | Growth under anaerobic condition | Reduction of nitrate |
|---|---|---|---|---|---|
| Bacillus polymixa | − | − | + | + | − |
| Bacillus macerans | − | − | + | + | |
| Bacillus circulans | − | − | + | + or − | |
| Bacillus sp. 38-2 | − | ± | + | ++ | + |
| Bacillus sp. No. 135 | − | − | ± | − | + |
| Bacillus sp. 169 | − | − | ± | − | − |
| Bacillus sp. No. 13 | + | + | ± | + | − |
| Bacillus sp. No. 17-1 | ++ | ++ | ++ | + | + |

From the above table it is noted that not only every species of Bacillus sp. No. 38-2, No. 135, No. 169, No. 13 and No. 17-1 has different characteristics from the known three species, but also they are not identical each other. Judging differences shown in the table, we concluded that every species of Bacillus sp. No. 38-2, Bacillus sp. No. 135, Bacillus sp. No. 169, Bacillus sp. No. 13 and Bacillus sp. No. 17-1 was identified as new species respectively as shown in U.S., Ser. No. 452,139.

The medium to be used for cultivation of the microorganism above described must be a basic medium containing carbonate, though it may be any of solid or liquid medium. Thus, a medium comprising essential components for growth of the microorganism, such as carbon source, nitrogen source, inorganic salt and the like and containing added carbonate is used. Starch, soluble starch and the like are used as the carbon source, Yeast extract, peptone, corn-steep liquor and the like are used as the nitrogen source. Thus a medium comprising soluble starch, peptone, yeast extract, $K_2HPO_4$, $MgSO_4 \cdot 7H_2O$ and an added carbonate is used. Any carbonate selected from anhydrous sodium carbonate, potassium carbonate, sodium bicarbonate and the like may be used.

It is very important to add a sufficient amount of carbonate to the medium to make the pH value of the medium alkaline.

The amount of the carbonate to be added to the medium is preferably in the range of 0.5% to 1.5% by weight. This fact was determined by the following experiments.

The experiments was carried out using a standard neutral medium comprising 5 gs. peptone, 5 gs. yeast extract, 20 gs. starch, 1 g $K_2HPO_4$, 0.2 g $MgSO_4 \cdot 7H_2O$, 15 gs. agar and 1 liter of water and modified media containing various salts and carbonates in amount shown in the Table 7.

Media having pH value of 10 was prepared by adding sodium hydroxide to the neutral medium.

Each of the media was innoculated with the strain of Bacillus sp. No. 17-1 and cultured with shaking at a temperature of 37° C.

Growth of the microorganism was observed by taking the culture broth after 18 hours into a cuvett of 1 cm and measuring the absorbance of light at 660 mμ.

The yield of cyclodextrin was determined by measuring the activity of the culture broth after 3 days cultivation under the condition described in later.

These results have been shown in the Table 7.

Table 7

| Medium salt added | pH before cultivation | Growth | Activity U/ml |
|---|---|---|---|
| Standard (no additive) | 7.0 | 0.6 | <1.0 |
| | 10.0 | 0.8 | <1.0 |
| 1% NaCl | 7.0 | 0.8 | <1.0 |
| | 10.0 | 0.8 | <1.0 |
| 1% KCl | 7.0 | 0.8 | <1.0 |

Table 7-continued

| Medium salt added | pH before cultivation | Growth | Activity U/ml |
|---|---|---|---|
| | 10.0 | 1.0 | <1.0 |
| $NaHCO_3$ | | | |
| 0.5% | 9.0 | 1.0 | 15 |
| 1.0% | 9.2 | 1.1 | 18 |
| 1.5% | 9.3 | 1.1 | 21 |
| 2.0% | 9.5 | 1.0 | 20 |
| $Na_2CO_3$ | | | |
| 0.5% | 9.6 | 1.1 | 16 |
| 1.0% | 10.0 | 1.1 | 22 |
| 1.5% | 10.2 | 1.2 | 22 |
| 2.0% | 10.5 | 1.0 | 20 |
| $K_2CO_3$ | | | |
| 0.5% | 9.8 | 1.1 | 14 |
| 1.0% | 10.2 | 1.1 | 21 |
| 1.5% | 10.3 | 1.0 | 22 |
| 2.0% | 10.5 | 1.1 | 20 |

From the results shown in the table, it is noted that the presence of suitable amount of the carbonate in the medium is an indispensable to produce the subject enzyme to be used in the present invention.

The cultivation of the microorganism described above can be carried out by means of conventional aerobic shaking culture or air bubbling culture. It is preferable to culture for 24–96 hours at a temperature between 30° C. and 37° C.

The resulted enzyme can be isolated from the culture broth by any conventional method. For example, when the cultivation is finished, the microorganism is removed from the culture broth and then after neutralization of the broth with acetic acid or the like or without any neutralization, the broth is treated with an organic solvent such as methanol or ammonium sulphate to precipitate enzyme and then the precipitated enzyme is separated from the liquid and dehydrated, thereby to obtain crude powdery enzyme. The resulted crude enzyme can be used for production of the cyclodextrin of the present invention as it is.

Purified enzyme can be obtained from the above crude enzyme as follows: The crude powdery enzyme is dissolved in water and the resulted solution is dialyzed against water overnight. The solution is passed through a column of diethyl aminoethyl cellulose (DEAE Cellulose) equilibrated with 0.01M Tris-HCl Buffer solution of pH 9.0. Thus the enzyme in the solution is completely adsorbed in the cellulose. The adsorbed enzyme is eluted by changing the concentration of NaCl in the buffer solution from 0.01M to 0.5M.

The active fractions are collected and concentrated. Then the concentrated solution is purified by gel-filtration chromatography using Sephadex G-75 and Sephadex G-100 ("Sephadex" is a resistered trade name) and the resulted cake is freez-dried, thereby to obtain a purified enzyme powder.

The activity of the resulted enzyme is determined as follows:

0.05 ml of the enzyme solution with a suitable concentration is mixed with 0.5 ml of 1% soluble starch solution in 0.1M glycine buffer (pH 10.5).

The resulted mixture is subjected to a temperature of 40° C. for 2 hours, after reaction has been completed the solution is neutralized with acetic acid and further heated at 100° C. for 10 minutes.

The resulted solution is mixed with 50 µg of glucoamylase, the solution is subjected to a temperature of 40° C. for one hour to decompose the residual starch and the amount of glucose produced in the solution is determined by means of the dinitrosalicylic acid method.

The same process is repeated except using water instead of the enzyme solution.

The difference of the determined amount of glucose shows the amount of the produced cyclodextrin.

One unit of the enzyme was defined as that amount of enzyme producing 1 mg of the cyclodextrin under the method described above.

The activity of the enzyme can be assayed by the iodine method as follows:

The enzyme solution (0.01 ml) which has been suitably diluted so as to reduce the absorbance at 700 mµ by from 10% to 20%, is mixed with 0.2 ml of 0.2% potato starch aqueous solution and 0.2 ml of 0.1M acetic acid buffer solution having pH value of 4.5, then the resulted mixture is heated at 40° C. for 10 minutes. After reaction, the resulted solution is mixed with 0.3 ml of 0.2M hydrochloric acid and then 3 ml of 0.005% iodine solution. The absorbance at 700 mµ of the sample is measured.

The physicochemical properties of the enzymes produced from Bacillus sp. No. 38-2 (ATCC 21783), Bacillus sp. No. 135 (ATCC 21595), Bacillus sp. No. 169 (ATCC 21594), Bacillus sp. No. 13 (ATCC 31006) and Bacillus sp. No. 17-1 (ATCC 31007) will be explained in detail.

I. Enzyme produced from Bacillus sp. No. 38-2 (ATCC 21783):

(1) Substrate Specificity:

The enzyme produced by cultivation of the above identified microorganism under the specific conditions described above is active to starch, and reduces the starch-iodine reaction. However, the enzyme does not increase reducing powder at pH 9.0 and it produces cyclodextrin. Thus, the enzyme has been determined to be a cyclodextringlycosyltransferase and to be a liquefying amylase.

(2) Optimum pH:

The optimum pH of the enzyme has been determined by measuring activity of the enzyme at various pH values by means of the method described above.

Each pH value has been achieved by use of the following buffers respectively.

| pH | Buffer solution |
|---|---|
| 4 – 5 | Acetate |
| 5 – 8.5 | Tris-maleate |
| 9 – 11 | Sodium hydroxyde |
| 11 – 12 | Sodium carbonate and sodium hydroxyde |

The sample of the enzyme has been previously desalted with Sephadex G-25.

The results obtained are shown in FIG. 1, in which the curve "a" shows yield of cyclodextrin at various pH values and the curve "b" shows relative activities of the amylase at various pH values.

From the curve "a", it is noted that optimum pH value for production of cyclodextrin lies 9.0 and from the curve "b" it is noted that the optimum pH value for production of amylase lies at 4.5, 7.0 and 9.0

(3) Stable pH:

The enzyme solution (0.01 ml) desalted with Sephadex is mixed with 0.1 ml of various kinds of buffer solution containing 1µ mole of $CaCl_2$ as a stabilizer.

The resulted mixture is heated at 60° C. for 30 minutes and then 0.2 ml of a buffer solution of pH 9.0 and 0.2 ml of a substrate are added to the mixture, thus the residual activity has been determined. The results are shown in the following Table 8.

Table 8

| pH | Buffer Solution | Residual Activity (%) |
|---|---|---|
| 4 | acetic acid | 0 |
| 5 | " | 12 |
| 6 | tris maleate | 100 |
| 7 | " | 100 |
| 8 | " | 100 |
| 10 | $Na_2CO_3$, $NaHCO_3$ | 70 |
| 11 | $Na_2CO_3$ | 10 |

It is clearly indicated that the enzyme is quite stable in the range of pH 6 to 8.

(4) Thermal Stability:

The thermal stability of the enzyme has been studied as follows:

The same enzyme solution in tris-maleate buffer of pH 8 as shown in the above paragraph (3) is prepared (no $Ca^{++}$). Said solution is hold at different temprature for different time of period and the residual activity has been determined.

The following results were obtained.

Table 9

| Temperature | Time Minutes | Residual Activity (%) |
|---|---|---|
| 50 | 15 | 100 |
| 50 | 30 | 100 |
| 55 | 15 | 80 |
| 60 | 15 | 10 |

(5) Inhibition by Temperature:

The same enzyme solution of pH 8 as shown in (3) is prepared and 5 m M of $Ca^{++}$ is added to the solution.

The solution is heated for 30 minutes varying the temperature as shown in the following table. The residual activities are determined and results obtained are shown in the following Table.

Table 10

| Temperature | Residual Activity, % | |
|---|---|---|
| | pH 4 | pH 9 |
| 50 | 100 | 100 |
| 55 | 100 | 100 |
| 60 | 100 | 100 |
| 65 | 100 | 100 |
| 70 | 61 | 65 |
| 75 | 10 | 10 |
| 80 | 0 | 0 |

From the above examination, we found that any increase of activation by addition of $Ca^{++}$ could not be observed, whereas the thermal stability had been improved.

(6) Purification of the Enzyme:

$CaCl_2$ (5 M) is added to the culture broth of Bacillus sp. No. 38-2 (ATCC 21783) to adjust the pH value to 10 and produced precipitates are removed by centrifuge. One-half acetone is added to the culture broth to form precipitates.

The resulted precipitates are collected and dissolved in water. After dialysis overnight, the solution is concentrated with polyethylene-glycol.

After gel-filtration chromatography with Sephadex G-100, active fractions are collected.

The enzyme has been adsorbed on DEAE cellulose column equilibrated with 10 m M of Tris-HCl buffer solution containing 1 m M $CaCl_2$ at pH 8.5 and then the adsorbed enzyme is eluted varying the concentration of $CaCl_2$ from 5 m M to 50 m M. Usually about 40 m M is used.

The active fractions are collected and purified by gel-filtration using Sephadex C-75, to obtain the final product.

Two curves showing the relation between the enzyme activity and the pH value which have been measured before and after purification are essentially the same.

(7) Homogeneity of the Enzyme:

The homogeneity of this enzyme has been proved by the following observations:
(i) Ultra centrifugal analysis gave a single peak of sedimentation constant at approximately 4.
(ii) A single peak of the activity was observed by gel-filtration chromatography.
(iii) Disc electrophoretic analysis at pH 8.3 shows monodisperse.
(iv) The ratio of the enzyme activity at pH values 4 and 9 does not change, even in the partially denatured enzyme by heating.

The comparison of the physicochemical properties of enzyme disclosed above and that of the known saccharifying and liquefying amylases produced from *Bacillus subtilis* (Ref.: "Advances in Applied Microbiology", 7, p. 293, 1965) is shown in the following Table 11.

cyclodextrin. Thus, the enzymes have been determined to be cyclodextrin-glycosyltransferase.

By paper chromatography of the products, small amount of a series of oligo-saccharides such as maltose, maltotriose, maltotetraose, etc. are observed. From the facts these enzymes have been determined to be liquefying amylases.

(2) Optimum pH:

The optimum pH of the enzymes produced from Bacillus sp. No. 135 and No. 169 have been determined by measuring activities at various pH values as described above.

The enzyme used has been previously desalted with Sephadex G-25. The other conditions have been disclosed above.

Each pH value used has been achieved by use of the following buffers respectively.

| pH | Buffer |
|---|---|
| 4 and 5 | Acetate |
| 6, 7 and 8 | Phosphate |
| 9 and 10 | Borate |
| 10, 11 and 12 | Glycine-NaOH—NaCl |

Figure 2:
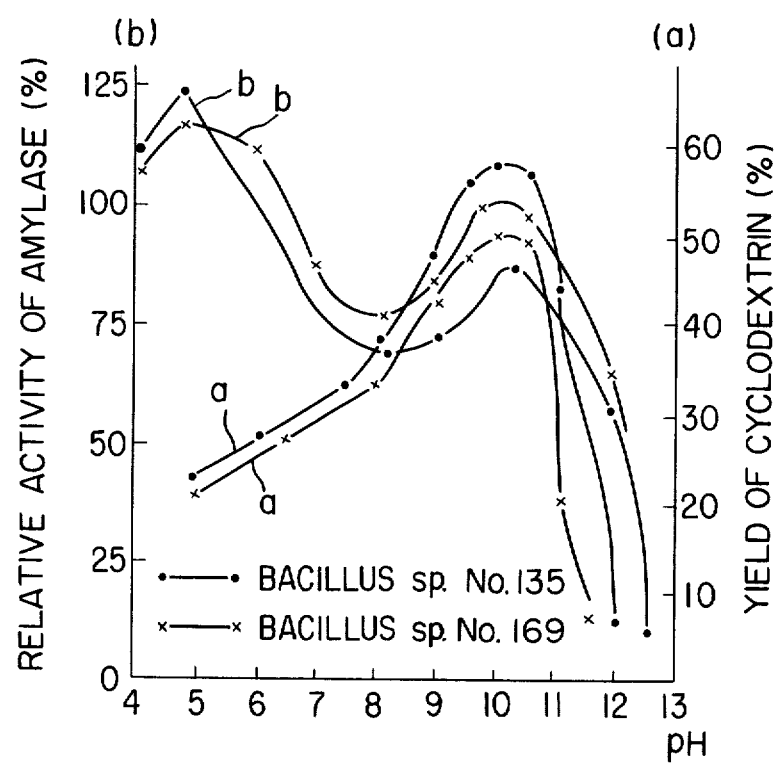
FIG. 2 illustrates the relation (curve a) between the ratio of production of cyclodextrin by the enzyme of this invention (fermentation product of Bacillus sp. No. 135 (ATCC 21595) and Bacillus sp. No. 169 (ATCC 21594)) and the pH, and the relation (curve b) between the amylase activity of said enzymes and the pH.

The results obtained are shown in FIG. 2, in which the curve "a" shows yield of cyclodextrin at various pH values and the curve "b" shows relative activities of the amylase at various pH values.

From the curve "a", it is noted that optimum pH value for production of cyclodextrin lies between 10 and 10.5 and from the curve "b" it is noted that the optimum pH value for production of amylase lies at 4.5.

(3) Stable pH:

The pH range in which the activity of the enzymes can be maintained in stable has been studied.

The enzyme (0.01 ml) which has been desalted with Sephadex is mixed with 0.1 ml of various kinds of buffer solutions containing 1.0μ mole of $CaCl_2$ as a stabilizer.

The resulting mixture is heated at 55° C. for 15 minutes and then 0.2 ml of a buffer solution having pH 10.5 and 0.2 ml of a substrate are added, thus the residual activity has been observed respectively.

The results of the test are shown in the following

Table 11

| Enzyme | Type | Thermal stability | Stable pH range | Optimum pH | Stabilization by Ca++ | Hydrolysis of starch |
|---|---|---|---|---|---|---|
| Amylase from *B.subtilis* | Liquefying | 65–90° C | 4.8–10.8 | 5.4–6.0 | + | 35% |
| | Saccharifying | 55–70° C | 4.0–7.8 | 4.8–5.2 | − | 70% |
| Amylase from *B. sp.* No. 38-2 (ATCC 21783) | Liquefying | 60–70° C (in the presence of Ca++) | 5–10 | 4.5 7.0 9.0 | + | 15% |

Note:
+ : stable
− : unstable

II. Enzymes produced from Bacillus sp. No. 135 (ATCC 21595) and Bacillus sp. No. 169 (ATCC 21594):

(1) Substrate Specificity:

The enzymes produced by cultivation of the above identified two microorganisms under the specific conditions described above are active to starch and reduce the starch-iodine reaction. However, increase of reducing activity at pH 10.5 is little, and the enzymes produce Table 12.

Table 12

| pH | Buffer | Residual Activity, % |
|---|---|---|
| 4 | Acetic acid | 0 |
| 6 | Tris maleate | 0 |
| 7 | | 25 |
| 8 | | 51 |
| 10 | $Na_2CO_3$—$NaHCO_3$ | 47 |

Table 12-continued

| pH | Buffer | Residual Activity, % |
|---|---|---|
| 11 | Na$_2$CO$_3$ . NaOH | 10 |

(4) Thermal Stability (Inactivation):

Each enzyme produced from Bacillus sp. No. 135 and No. 169 has lost activity about 50 to 70% by heating at a temperature of 60° C. for 10 minutes at pH 10.0.

Whereas at 50° C. for 15 minutes any activity is not lost.

(5) Inhibition, Activation and Stabilization:

The same enzyme solution of pH 10 as disclosed in (3) is prepared and different amount of Ca$^{++}$ is added to the solution. The solution is heated to 55° C. for 15 minutes. The residual activation is determined and shown in the following Table 13.

Table 13

| Amount of Ca$^{++}$ | Residual Activity |
|---|---|
| 0 | 0 |
| 0.15μ mole | 0 |
| 0.25μ mole | 10 |
| 0.5μ mole | 25 |
| 1.0μ mole | 54 |
| 1.5μ mole | 40 |

From the above examination, we found that any increase of activation by addition of Ca$^{++}$ could not be observed, whereas the thermal stability had been improved.

Judging the physicochemical properties of the enzymes from Bacillus sp. No. 135 and 169, these enzymes have characteristic by the fact that they have the optimum pH 10.5.

Thus, we confirmed that these enzymes are novel amylases.

III. Enzyme produced from Bacillus sp. No. 13 (ATCC 31006):

(1) Substrate Specificity:

The enzyme produced by cultivation of the above identified microorganism under the specific conditions described above is active to starch and reduces the starch-iodine reaction. However, the enzyme does not increase reducing power at pH 10.5 and it produces cyclodextrin. Thus, the enzyme has been determined to be a cyclodextrin-glycosyl-transferase and also to be a liquefying amylase. The amylase reduces starch-iodine reaction and increases the reducing power at pH 4.5.

(2) Optimum pH:

The optimum pH of the enzyme has been determined by measuring activities and yield of cyclodextrin at various pH values by means of the above described method.

Each pH value has been achieved by use of the following buffers respectively.

| pH | Buffer |
|---|---|
| 4 - 5 | Acetate |
| 5 - 8.5 | Tri maleate |
| 9 - 11 | Glycine—NaOH |
| 11 - 12 | NaHCO$_3$—NaOH |

The sample of the enzyme has been previously desalted with Sephadex G-25.

Figure 3:
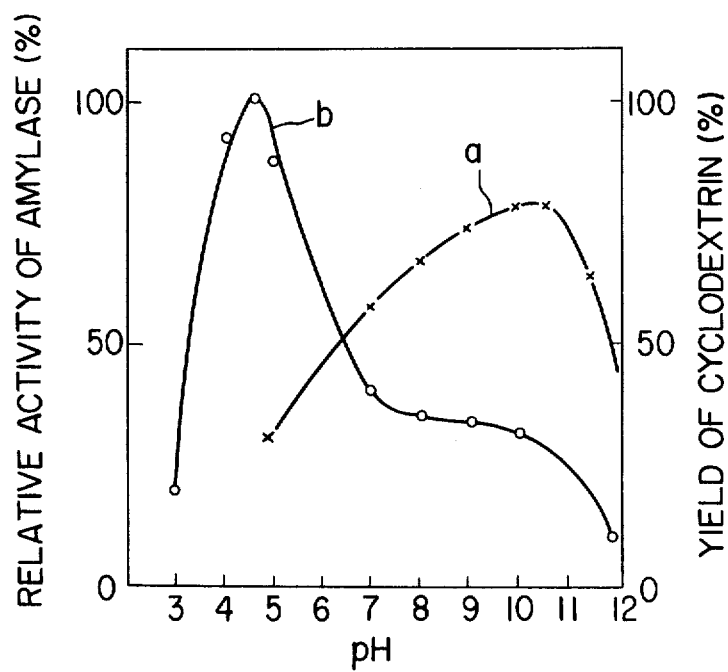
FIG. 3 illustrates the relation (curve a) between the ratio of production of cyclodextrin by the enzyme of this invention (fermentation product of Bacillus sp. No. 13 (ATCC 31006) and the pH, and the relation (curve b) between the amylase activity of said enzyme and the pH.

The results obtained are shown in FIG. 3, in which the curve "a" shows yield of cyclodextrin at various pH values and the curve "b" shows relative activities of the amylase at various pH values.

From the curve "a", it is noted that optimum pH value for production of cyclodextrin lies between 10 and 10.5 and from the curve "b" it is noted that the optimum pH value for production of amylase lies at 4.5.

(3) Stable pH:

The pH range in which the activity of the enzyme can be maintained in stable has been studied.

The enzyme solution (0.01 ml) desalted with Sephadex is mixed with 0.1 ml of a buffer solution listed in the following table and the mixture is heated at 50° C. for 10 minutes. Then 0.2 ml of Buffer solution of pH 10.0 and 0.2 ml of substrate are added to the heated solution. Thus the residual activities at various pH values are observed. The results obtained are shown in the following Table.

Table 14

| pH | Buffer | Residual Activity, % |
|---|---|---|
| 4 | Acetate | 0 |
| 5 |  | 10 |
| 6 |  | 60 |
| 7 | Tris maleate | 65 |
| 8 |  | 80 |
| 10 | Na$_2$CO$_3$ . NaHCO$_3$ | 60 |
| 11 | Na$_2$CO$_3$ | 10 |

(4) Thermal Stability (Conditions for Inactivation):

The thermal stability of the enzyme has been studied.

The same enzyme solution of pH 7 as shown in the above paragraph (3) is prepared. The inactivation of the solution has been observed by keeping the solution at various temperature for 10 minutes respectively.

The results obtained are shown in the following Table 15.

Table 15

| Temperature °C | Time Minutes | Residual Activity, % |
|---|---|---|
| 45 | 10 | 100 |
| 50 | 10 | 80 |
| 55 | 10 | 40 |
| 60 | 10 | 5 |

(5) Inhibition, Activation and Stabilization:

The same enzyme solution of pH 7 as disclosed in (3) is prepared.

Various amount of Ca$^{++}$ is added to the solution and the increase of the activity has been studied. Any increase has not been observed.

Then the thermal stability of same solution has been studied by heating the solution containing 5 mM Ca$^{++}$ at different temperature for 20 minutes and measuring the residual activity of the solution. The results obtained are shown in the following Table 16.

Table 16

| Temperature °C | Residual Activity, % |
|---|---|
| 50 | 100 |
| 55 | 80 |
| 60 | 20 |
| 65 | 5 |
| 70 | 0 |

Table 16-continued

| Temperature °C | Residual Activity, % |
|---|---|
| 75 | 0 |
| 80 | 0 |

(6) Purification of the Enzyme:

$CaCl_2$ (5 M) is added to a culture broth of the microorganism to form precipitates and which are removed from the liquid by centrifugation. A half volume of acetone is added to the filtrate to form precipitates.

The resulted precipitates are collected and dissolved in water. After dialysis overnight the solution is concentrated with polyethylene glycol.

After gel-filtration chromatography with Sephadex G-100, active fractions are collected. The enzyme is adsorbed on DEAE cellulose column equilibrated with 10 m M of tris-HCl buffer solution of pH. 9.0 containing 10 m M $CaCl_2$ and then the adsorbed enzyme is eluted by varying the concentration of NaCl from zero to 0.5 M. Usually the enzyme can be eluted at the concentration of about 0.1 M.

Active fractions are collected, the collected solution is gel-filtrated with Sephadex G-75 to obtain the final product.

Two curves showing the relation between the enzyme activity and the pH value which have been measured before and after purification are substantially same.

(7) Range of Working Temperature:

The activity of the enzyme has been measured at various temperatures and we found that the optimum working temperature of the enzyme is in the range of from 45° C. to 50° C.

(8) Molecular Weight of the Enzyme:

The molecular weight of the enzyme is determined by means of Gel-filtration method and found being about 60,000.

(9) Isoelectric Point:

The isoelectric point of the enzyme has been examined by means of the electrophoresis using filter paper and found that it is about 4.5.

(10) Elementary Analysis:

C: 47.8%, H: 7.2%, S: 0.6%, N: 15.4%, Ash: 0.9%.

IV. Enzyme produced from Bacillus sp. No. 17–1 (ATCC 31007):

(1) Substrate Specificity:

The enzyme produced by cultivation of the above identified microorganism under the specific conditions described above is active to starch and reduces the starch-iodine reaction. However, any increase of reducing power can not be observed.

The almost all of the final products of the enzyme is found to be cyclodextrin.

(2) Optimum pH:

The optimum pH of the enzyme has been determined by measuring activity of the enzyme at various pH values by means of the above described method.

Each pH value listed has been achieved by use of the following buffers respectively:

| pH | Buffer |
|---|---|
| 4, 5 | Acetate |
| 6, 7, 8 | Phosphate |
| 9, 10 | Borate |
| 10, 11, 12 | Glycine—NaOH—NaCl |

The sample of the enzyme has been previously desalted with Sephadex G-25.

Figure 4:
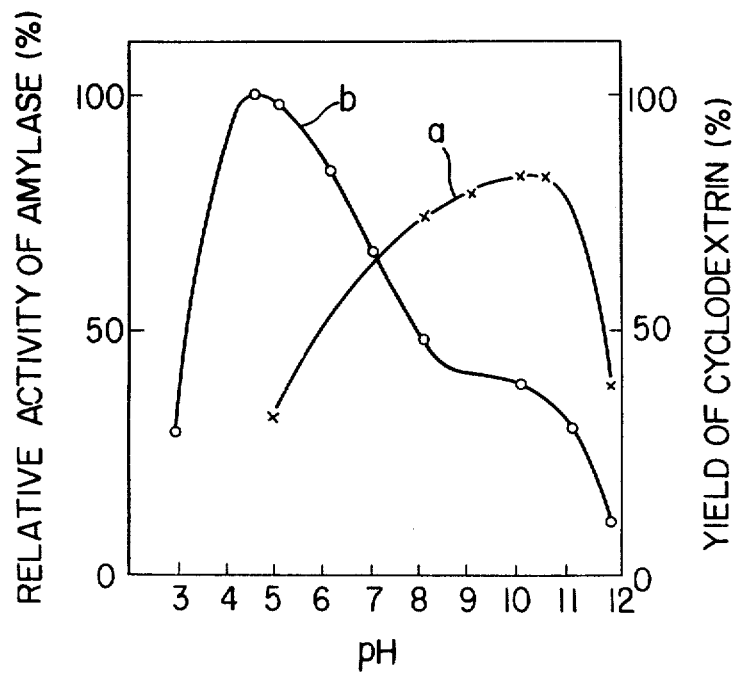
FIG. 4 illustrates the relation (curve a) between the ratio of production of cyclodextrin by the enzyme of this invention (fermentation product of Bacillus sp. No. 17-1 ATCC 31007) and the pH and the relation (curve b) between the amylase activity of said enzyme and the pH.

The results obtained are shown in FIG. 4, in which the curve "a" shows yield of cyclodextrin at various pH values and the curve "b" shows relative activities of the amylase at various pH values.

From the curve "a", it is noted that the optimum pH value for production of cyclodextrin lies between 10 and 10.5 and from the curve "b" it is noted that the optimum pH value for production of amylase lies at 4.5.

(3) Stable pH:

The pH range in which the activity of the enzyme can be maintained in stable has been studied.

The enzyme solution (0.01 ml) desalted with Sephadex is mixed with 0.1 ml of a buffer solution listed in the following table and the mixture is heated at 55° C. for 10 minuted. Then 0.2 ml a buffer solution of pH 10.5 and 0.2 ml of substrate are added to the heated solution. Thus the residual activities at various pH values are observed. The results obtained are shown in the following Table 17.

Table 17

| pH | Buffer | Residual Activity, % |
|---|---|---|
| 4 | Acetic acid | 0 |
| 6 | Tris maleate | 40 |
| 7 | " | 70 |
| 8 | " | 95 |
| 10 | $Na_2CO_3$—$NaHCO_3$ | 80 |
| 11 | $Na_2CO_3$—NaOH | 20 |

(4) Thermal Stability (Conditions for Inactivation):

About 20–30% of the activity of the enzyme has been lost by heating at 55° C. for 10 minutes at pH 10 and almost all of activity has been lost by heating at 60° C. for 10 minutes.

(5) Inhibition, Activation and Stabilization:

We examined the influence of addition of $Ca^{++}$ on increase of the enzyme activity. No increase of the activity can be found, but the thermal stability has been improved by addition of $Ca^{++}$.

Thus an enzyme solution having pH 10 is prepared and the solution is heated at 55° C. for 20 minutes, and the residual activity has been examined by varying the amount of $Ca^{++}$ in the solution.

The results are shown in the following Table 18.

Table 18

| Amount of added $Ca^{++}$, μ mole | Residual Activity, % |
|---|---|
| 0 | 30 |
| 0.15 | 40 |
| 0.25 | 60 |
| 0.5 | 80 |
| 1.0 | 100 |
| 1.5 | 100 |

(6) Purification:

Purification of the enzyme can be carried out by the same method described in the purification of the enzyme from Bacillus sp. No. 13 (ATCC 31006).

(7) Range of Working Temperature:

The enzyme activity has been measured at various temperatures and we found that the optimum working temperature of the enzyme lies in the range of 50° C. to 55° C.

(8) Molecular Weight:

The molecular weight by gel-filtration method has been found to be about 50,000 to 60,000.

(9) Isoelectric Point:

The isoelectric point of the enzyme has been examined by means of the Ampholine electro-focusing method and we found that it is at pH 4.5.

(10) Elementary Analysis:

C: 48.0%, H: 7.3%, S: 0.65%, N: 15.7%, Ash: 1.01%.

Summing physicochemical properties of amylases produced from Bacillus sp. No. 38-2 (ATCC 21783), Bacillus sp. No. 135 (ATCC 21595), Bacillus sp. No. 169 (ATCC 21594), Bacillus sp. No. 13 (ATCC 31006) and Bacillus sp. No. 17-1 (ATCC 31007), these Amylases are characteristic in that they have the optimum pH value for producing cyclodextrin in the range of from 9 to 10.5, particularly from 10 to 10.5. Further we found that these amylase was characteristic in that the ratio of relative activities at pH 4.5 and pH 10 was specific as shown in the Table 19.

Table 19

| Species | Optimum pH of cyclodextrin glycosyl-transferase | Ratio of amylase activities (relative activity) at | |
|---|---|---|---|
| | | pH 4.5 | pH 10 |
| B.sp.No.13 (ATCC 31006) | 10 – 10.5 | 100% | 30 – 50% |
| B.sp.No.17-1 (ATCC 31007) | 10 – 10.5 | 100% | 40 – 50% |
| B.sp.No.38-2 (ATCC 21783) | 9 – 9.5 | 100% | 70 – 80% |
| B.sp.No.135 (ATCC 21595) | 10 – 10.5 | 100% | 80% |
| B.sp.No.169 (ATCC 21594) | 10 – 10.5 | 100% | 80% |

The invention of the present application relates to a process for producing cyclodextrin characterized by use of a specific alkaline amylase under specific pH conditions.

The alkaline amylase to be used must be selected from amylases having the optimum pH value within the range of from 7 to 10.5, preferably from 8 to 10.5, more preferably from 10 to 10.5.

The preferable amylase is a cyclodextrin glycosyl-transferase having the optimum pH value of from 8 to 10.

The alkaline amylase to be used is preferably selected from amylases produced by cultivation of a microorganism selected from the group consisting of Bacillus sp. No. 38-2 (ATCC 21783), Bacillus sp. No. 135 (ATCC 21595), Bacillus sp. No. 169 (ATCC 21594), Bacillus sp. No. 13 (ATCC 31006) and Bacillus sp. No. 17-1 (ATCC 31007).

The pH condition to be used according to the present invention shall be within the range of pH 6 to 10.5, particularly within the range of pH 9.0 to 10.5.

According to the present invention, any kinds of starch may be used, and a preferable starch is potato-starch.

The process of the present invention can be carried out as follows:

Starch is gelatinized, preferably by NaOH. After adjusting the pH value of the starch to 6.0–10.5, preferably to 9.0–10.5, the alkaline amylase disclosed above is added to the starch and the solution is maintained at the optimum working temperature for sufficient time to produce cyclodextrin. The optimum working temperature depends on the kind of the alkaline amylase used as described above. The production of cyclodextrin can usually be accomplished during twelve hours.

More specifically, the pH of the starting starch liquid is adjusted to about 10 and the starch is gelatinized and cooled. Then, an alkaline amylase produced by the above-mentioned microorganism is added to the gelatinized starch to cause reaction. Then, the reaction mixture liquid is heated to deactivate the enzyme, and the liquid is cooled and the pH is adjusted to about 5.0. Then, a commercially available glucoamylase is added to the reaction liquid to decompose unreacted starch. The reaction mixture liquid is then filtered and concentrated to elevate the cyclodextrin content to at least about 40%, and a small amount of cyclodextrin is added as a seed to the liquid. When the liquid is allowed to stand still, cyclodextrin is precipitated and let sediment. The precipitate is recovered by filtration and dried to obtain the intended cyclodextrin in a high yield (50 to 70%).

In this preferred embodiment, since the amylase has an optimum pH on the alkaline side, it is necessary that the pH should be adjusted to about 6.0 to about 10.5, especially about 9.0 to about 10.5. Any of commercially available glucoamylases can be added to the reaction liquid, and the kind of the cyclodextrin to be added as a seed in a small amount is not particularly critical. At the concentration step, it is necessary that the reaction liquid should be concentrated so that the cyclodextrin content is at least about 40%. According to this process, it is possible to obtain the intended cyclodextrin in such a high yield as exceeding about 50%.

We have confirmed that the cyclodextrin obtained according to the process of the present inventionn has the same physicochemical properties as that of the known cyclodextrin.

The physical and chemical properties of the cyclodextrin of the present invention are as follows:

1. Elementary Analysis:

C: 44.4%, H: 6.1%, O: 49.5%.

2. Molecular Weight:
   Crude Product: 1200 ± 100
   α-dextrin Fraction: 970
   β-dextrin Fraction: 1,140
   γ-dextrin Fraction: 1,300

3. Melting Point:

200° C. (as acetylated)

4. Optical Rotation [α]D:

α-dextrin Fraction: +150
   β-dextrin Fraction: +160
   γ-dextrin Fraction: +170

5. Ultraviolet Absorption Spectrum:

No characteristic

6. Infra-red Absorption Spectrum:

Almost same as that of commercially availabe α-dextrin.

7. Color Reaction:

α-dextrin Fraction:give blue color by iodine
β,γ-dextrin Fraction:hardly iodine reaction, give yellowish brown or reddish brown color.

8. Crystallography:

α-dextrin fraction: Hexagon or blade
β-dextrin fraction: Parallelogram
γ-dextrin fraction: Quadrilateral 9. Acidity:
Neutral 10. Color:
White 11. Reducing Power:

No reducing power.

Glucose, maltose and malt-triose are produced by Taka-α-amylase. But no effect by an enzyme which decomposes poly or oligosuccharides from the chain termini.

As disclosed above, the cyclodextrin produced according to the process of the present invention contains α, β and γ, especially, β cyclodextrin fractions.

The enzymes to be used according to the present invention have better thermal stability higher by 15° C. to 20° C. than that of the known cyclodextrin producing enzyme. Therefore the process of the present invention is extremely useful and effective.

The cyclodextrin produced by the process of the present invention has various uses. Particularly it is useful as a substitute product for gum arabic or for the manufacture of sweetenings such as millet jelly and so on, because the cyclodextrin glucosyltransferase has transferase activity.

For instance, a novel and useful sweetening can be produced as follows:

10 gs. of cyclodextrin and starch is mixed with 3 gs. of sucrose and the mixture is dissolved in water. 100 ml of the enzyme solution containing cyclodextrin-glucosyltransferase is added to the solution and the solution is allowed to stand at a temperature of 37° C. overnight.

The solution is concentrated to obtain 10 gs. or a syrup like millet jelly. We found that the product comprises minor sucrose and major compound of sucrose and glucose and has sufficient sweetness for the sweetening.

The invention will be explained by the following examples, but we do not intend to restrict the invention by them.

EXAMPLE 1

The pH of 15 liter of water containing 4% (w/v) of potato starch (D.S. amount: 600 g) was adjusted to 10 by sodium hydroxide, and the liquid was heated at 125° C. for 30 minutes to gelatinize the starch. The gelatinized starch was cooled to 50° C., and 600 mg of an alkaline amylase produced from the above-mentioned Bacillus sp. No. 38-2 (ATCC 21783) was added to the starch and reaction was conducted at 50° C. for 30 hours.

After the reaction, the reaction mixture was heated at 100° C. for 5 minutes to deactivate the enzyme, and the mixture was cooled to 55° C. and the pH was adjusted to 5.0 by hydrochloric acid. Then, 900 mg of a glucoamylase (product sold under the tradename of GAS-1 by Amano Seiyaku K.K. and having an activity of 2000 units per gram) was added to the reaction mixture and reaction was carried out for 20 hours. Then, the reaction mixture was decolorized by active carbon and filtered according to customary procedures. The reaction mixture was then concentrated so that the solid content was elevated to 65%, and a small amount of cyclodextrin was added to the concentrate and it was allowed to stand still overnight in a cold chamber.

The resulting precipitated cyclodextrin was recovered by filtration and dried under reduced pressure to obtain 280 g of cyclodextrin.

EXAMPLE 2

The pH of 15 liter of water containing 4% (w/v) of potato starch (D.S. amount: 600 g) was adjusted to 9.5 by sodium hydroxide, and the liquid was heated at 125° C. for 30 minutes to gelatinize the starch. The gelatinized starch was cooled to 50° C., and 600 mg of an alkaline amylase produced from the above-mentioned Bacillus sp. No. 17-1 (ATCC 31007) was added to the starch and reaction was conducted at 50° C. for 30 minutes.

The reaction mixture liquid was treated in the same manner as in Example 1 to obtain 225 g of a precipitate of cyclodextrin.

EXAMPLE 3

The treatment was conducted in the same manner as in Example 1 except that the above-mentioned Bacillus sp. No. 13 (ATCC 31006), Bacillus sp. No. 135 (ATCC 21595) and Bacillus sp. No. 169 (ATCC 21594) were used instead of the above-mentioned Bacillus sp. No. 38-2 (ATCC 21783), to obtain cyclodextrin in yields of 220 g, 215 g and 217 g, respectively.

The following comparative test 1 is the result in the production of cyclodextrin by means of amylase obtained by cultivating *Bacillus macerans* according to the reference cited in the specification of U.S. Pat. No. 3,425,910, column 1, lines 39–41, wherein the crystallization and precipitation of cyclodextrin were conducted according to the process of the present invention:

COMPARATIVE TEST 1

15 liters of a 4% (w/v) solution of potato starch (containing 600 gr. of starch) was adjusted to pH 5.5, and then homogenized and changed to paste for heating at 125° C. for 30 minutes, and the obtained paste solution was rapidly cooled to 40° C. Separately 150 gr of finely chopped potatoes were added with 15 gr of calcium carbonate and 800 ml of water, then sterilized by heating at 120° C. for 30 minutes. After cooling, the potatoes were inoculated with *Bacillus macerans* and subjected to shakshaking cultivation at 37° C. for approximately 2 weeks. Then the bacteria were eliminated by filtration, and the filtrate was employed as the enzyme solution. 15 liters of thus obtained enzyme solution was added to the above-mentioned paste solution, and, after reaction for 70 hours, amylase was deactivated by heating at 100° C. for 5 minutes. (In this state the amount of cyclodextrin was 32% with respect to that of starch).

The solution was successively cooled to 55° C., then added with hydrochloric acid to adjust the pH to 5.0, further added with 900 mg of glucoamylase (Amano Seiyaku Co., Ltd. tradename GSA-1; 2,000 units/gr), and subjected to reaction for 20 hours.

After the reaction the solution was treated with active charcoal and filtered in the ordinary manner, then it is concentrated to a solid content of 65%, and allows to stand overnight in a refrigerator with an addition of a small amount of cyclodextrin.

As a result, it was confirmed that the crystals of cyclodextrin were 6 gr (yield: 1%).

As indicated by the above-mentioned experimental result, it was confirmed that the addition of cyclodextrin as a seed at the crystallization and precipitation step of cyclodextrin is not at all effective in the production of cyclodextrin by means of amylase derived from *Bacillus macerans*.

The following comparative test 2 is the result of the production of cyclodextrin using the enzyme produced by the cyclodextrin-glycosyltransferase (Bacillus sp. No. 38-2 (ATCC 21594) of the method of the present invention), in accordance with the method disclosed in Example I of the specification of the U.S. Pat. No. 3,425,910.

COMPARATIVE TEST 2

To a 30% by weight suspension of potato starch at pH 7.2 was added the bacterial α-amylase preparation (Crystase (10,000 units/g): proprientary name of a bacterial α-amylase preparation produced and marketed by Daiwa Kasei Kogyo Co.) at a concentration of 0.1% of the enzyme preparation by weight on a starch solids basis.

The suspension was gradually added, during a 30 minutes period, to a vessel maintained at a temperature of 88°-92° C. Agitation was continuous and the temperature maintained for an additional 10 minutes until the starch was partially hydrolyzed to 1.8 DE. The hydrolyzed starch was then immediately adjusted to pH 8.5, heated to 130° C. and held 15 minutes to destroy the residual α-amylase activity.

The starch hydrolysate thus obtained was then cooled to 65° C., and the pH was adjusted to 8.5. The hydrolysate was then converted in the presence of 5 milliliters of toluene per 100 milliliter of conversion liquor with an amount of cyclodextrin with an amount of cyclodextrin transglycosylate produced from Bacillus sp. No. 38-2 (ATCC 21594) equivalent to 10,000 units per 100 grams of starch hydrolysate solids. After 30 hours of enzymolysis at 65° C., the conversion liquor was heated to boiling for 15 minutes to inactivate the enzyme and to drive off the toluene and solubilize the cyclodextrin. The conversion product was then filtered while hot.

The filtered conversion liquor was divided into three fractions, A, B, and C, and treated as described in the specification of U.S. Pat. No. 3,425,910.

The results of these operations are tabulated below.

| Portion Description | D.E. | CD Yield (%) |
|---|---|---|
| A — Original conversion liquor | 1.8 | 72 |
| B — α-Amylase treated liquor | 8.5 | 71 |
| C-1 — Crystalline cyclodextrin | — | 65 |
| C-2 — Concentrated mother liquor | 26.2 | 6 |

The results indicate that the yield of C.D. in the portion C-1 is 65% i.e., the pure cyclodextrin is 90% with respect to 72% of the portion A. With the method of the patent, on the other hand, the yield in the portion C-1 is 27%, which is only 69% with respect to 39% in the portion A.

This is based on a particular activity of the cyclodextrin-glycosyltransferase of the method of the present invention, and which proves an excellent feature of the method of the present invention which is capable of precipitating and sedimenting the object cyclodextrin advantageously simply by adding a seed of cyclodextrin, using a gelatinized starch as a starch and without at all using a precipitating agent such as toluene.

It is described in U.S. Pat. No. 3,425,910 that a 34% by weight solid content partially hydrolyzed starch solution can be converted with a 50% yield of cyclodextrin (column 3, line 3–5) and that high solid conversions are not prectical when the substrate consists of gelatinized, unhydrolyzed starch (column 7, line 5–8). The term "solid content" mentioned in the above means weight (g) of liquefied starch per 100 ml. In the case of gelatinized starch, the yield of cyclodextrin is considerably lowered at high or low content of liquefied starch as shown in Table II of said citation. This is due to poor dispersion of gelatinized starch in a high concentration which causes insufficient enzyme reaction and makes the precipitation of cyclodextrin difficult at a low concentration of gelatinized starch.

In the present invention good results are obtained even at low concentration of gelatinized starch as shown in Examples 1 and 2. Namely, in the data shown in said example, 4g of gelatinized starch per 100 ml is used and a good result can be obtained. The comparison mentioned above depends on the experiments using precipitant in the conventional methods and using seed of crystal of cyclodextrin in the present invention.

Therefore it is apparent from the above that better yields are obtained by the present invention using seeds than in the said patent using precipitant even at low concentration of gelatinized starch, and it is apparent that much higher yield is obtained by the present method than by a conventional method, because the yield of this invention is obtained by using seeds, not by precipitant, and then the actual amounts of produced cyclodextrin is much higher than the yield obtained by the prior art method a low concentration of gelatinized starch.

We claim:

1. A process for producing cyclodextrin in pure crystalline form from starch which comprises preparing a a solution of non-liquefied, gelatinized starch, as a starting material, adjusting the pH thereof to 6–10.5, adding thereto a cyclodextrin glycosyl transferase which has optimum pH in the alkaline side and which has been obtained by fermentation of an alkalophilic microorganism belonging to the genus bacillus and allowing cyclodextrin to be produced, filtering the reaction mixture, adding to the filtrate a glucoamylase to decompose unreacted starch contained in the filtrate, decomposing the unreacted starch with glucoamylase, concentrating the resulting filtrate to give a cyclodextrin concentrate containing cyclodextrin in an amount above 40% and adding a small amount of crystals of cyclodextrin as a seed to said concentrate to crystallize out cyclodextrin in pure crystalline form.

2. A process according to claim 1, wherein the alkalophilic microorganism belonging to the genus bacillus is selected from the group consisting of Bacillus sp. No. 38-2 (ATCC 21783), Bacillus sp No. 135 (ATCC 21595), Bacillus sp. No. 169 (ATCC 21594), Bacillus sp No. 13 (ATCC 31006), and Bacillus sp. No. 17-1 (ATCC 31007).

3. A process according to claim 1 wherein the pH of the starting material is adjusted to 9–10.5.

* * * * *

UNITED STATES PATENT OFFICE
CERTIFICATE OF CORRECTION

Patent No. 4,135,977　　　　　　　　　　Dated January 23, 1979

Inventor(s) Koki HORIKOSHI et al

It is certified that error appears in the above-identified patent and that said Letters Patent are hereby corrected as shown below:

Column 1, line 31, delete "(ATCC 21594)" and substitute therefor:--(ATCC 21783)--

Column 6, line 64, delete "trahalose" and substitute therefor:--trehalose--

Column 25, line 47, delete "(ATCC 21594)" and substitute therefor:--(ATCC 21783)--

Signed and Sealed this

Twenty-sixth Day of June 1979

[SEAL]

Attest:

RUTH C. MASON
*Attesting Officer*

DONALD W. BANNER
*Commissioner of Patents and Trademarks*